United States Patent
Fung et al.

(10) Patent No.: US 6,482,999 B2
(45) Date of Patent: Nov. 19, 2002

(54) METHOD FOR IMPROVING LIGHT OLEFIN SELECTIVITY IN AN OXYGENATE CONVERSION REACTION

(75) Inventors: Shun C. Fung, Bridgewater, NJ (US); James R. Lattner, Seabrook, TX (US); Stephen N. Vaughn, Kingwood, TX (US); Richard B. Hall, Whitehouse Station, NJ (US); Hsiang-Ning Sun, Drexel Hill, PA (US); Ron G. Searle, Houston, TX (US); Luc R. M. Martens, Meise (BE)

(73) Assignee: ExxonMobil Chemical Patents, Inc., Houston, TX (US)

( * ) Notice: Subject to any disclaimer, the term of this patent is extended or adjusted under 35 U.S.C. 154(b) by 0 days.

(21) Appl. No.: 09/251,142

(22) Filed: Feb. 17, 1999

(65) Prior Publication Data

US 2002/0013505 A1 Jan. 31, 2002

(51) Int. Cl.$^7$ .............................................. C07C 1/207
(52) U.S. Cl. ........................ 585/640; 585/642; 585/905; 585/906
(58) Field of Search ................................ 585/640, 642, 585/905, 906

(56) References Cited

U.S. PATENT DOCUMENTS

| | | | |
|---|---|---|---|
| 2,388,929 A | 11/1945 | Mottern ........................ 260/682 |
| 3,221,073 A | 11/1965 | Davis et al. ................... 260/677 |
| 4,058,576 A | 11/1977 | Chang et al. ................. 260/673 |
| 4,071,573 A | 1/1978 | Owen et al. ............. 260/668 R |
| 4,072,732 A | 2/1978 | Hargis et al. ................. 260/682 |
| 4,072,733 A | 2/1978 | Hargis et al. ................. 260/682 |
| 4,083,888 A | 4/1978 | Caesar et al. ................. 200/682 |
| 4,083,889 A | 4/1978 | Caesar et al. ................. 260/682 |
| 4,138,440 A | 2/1979 | Chang et al. ................. 260/668 |
| 4,328,384 A | 5/1982 | Daviduk et al. ............. 585/469 |
| 4,338,475 A | 7/1982 | Pennington et al. ......... 585/408 |
| 4,379,123 A | 4/1983 | Daviduk et al. ............. 422/142 |
| 4,396,789 A | 8/1983 | Barrocas et al. ............. 585/639 |
| 4,423,274 A | 12/1983 | Daviduk et al. ............. 585/640 |
| 4,431,856 A | 2/1984 | Daviduk et al. ............. 585/640 |
| 4,433,188 A | 2/1984 | Hoelderich et al. ......... 585/640 |
| 4,440,871 A | 4/1984 | Lok et al. .................... 502/214 |
| 4,449,961 A | 5/1984 | Forbus et al. ................ 585/640 |
| 4,499,327 A | 2/1985 | Kaiser ........................ 585/640 |
| 4,547,616 A | 10/1985 | Avidan et al. ................ 585/640 |
| 4,560,537 A | 12/1985 | Tabak ........................ 422/190 |
| 4,579,999 A | 4/1986 | Gould et al. ................. 585/640 |
| 4,590,320 A | 5/1986 | Sapre ........................ 585/324 |
| 4,665,268 A | 5/1987 | Lee et al. .................... 585/640 |
| 4,677,242 A | 6/1987 | Kaiser ........................ 585/638 |
| 4,677,243 A | 6/1987 | Kaiser ........................ 585/638 |
| 4,689,205 A | 8/1987 | Gould et al. ................. 422/146 |
| 4,752,651 A | 6/1988 | Kaiser ........................ 585/640 |
| 4,849,575 A * | 7/1989 | Lewis ........................ 585/640 |
| 4,861,938 A | 8/1989 | Lewis et al. ................. 585/640 |
| 4,873,390 A | 10/1989 | Lewis et al. ................. 585/638 |
| 4,899,002 A | 2/1990 | Harandi et al. ............. 585/312 |
| 4,912,281 A | 3/1990 | Wu ............................. 585/640 |
| 4,973,792 A | 11/1990 | Lewis et al. ................. 585/638 |
| 5,028,400 A | 7/1991 | Harandi et al. ............. 422/211 |
| 5,045,287 A | 9/1991 | Harandi et al. ............. 422/141 |
| 5,059,738 A | 10/1991 | Beech, Jr. et al. .......... 585/469 |
| 5,095,163 A | 3/1992 | Barger ........................ 585/640 |
| 5,126,308 A | 6/1992 | Barger et al. ................ 502/214 |
| 5,157,181 A | 10/1992 | Stine et al. .................. 585/329 |
| 5,177,283 A | 1/1993 | Ward ........................ 585/446 |
| 5,191,141 A | 3/1993 | Barger et al. ................ 585/640 |
| 5,414,181 A | 5/1995 | Bearden, Jr. et al. ....... 585/654 |
| 5,447,622 A | 9/1995 | Kerby et al. ................. 208/78 |
| 5,510,559 A | 4/1996 | Barger et al. ................ 585/664 |
| 5,714,662 A | 2/1998 | Vora et al. ................... 585/640 |
| 5,714,663 A | 2/1998 | Serrand et al. ............. 585/648 |
| 5,744,680 A | 4/1998 | Mulvaney, III et al. ..... 585/640 |
| 5,811,621 A | 9/1998 | Van Dijk .................... 585/634 |
| 5,817,906 A | 10/1998 | Marker et al. ............. 585/640 |
| 5,912,393 A | 6/1999 | Barger et al. ................ 585/640 |
| 5,914,433 A | 6/1999 | Marker ........................ 585/313 |
| 6,166,282 A | 12/2000 | Miller ........................ 585/638 |

FOREIGN PATENT DOCUMENTS

| | | |
|---|---|---|
| CA | 1 130 820 | 8/1982 |
| CA | 1 196 031 | 10/1985 |
| EP | 088 494 | 9/1983 |
| EP | 091 751 | 10/1983 |
| EP | 359841 * | 3/1990 |
| EP | 882 692 | 12/1998 |

OTHER PUBLICATIONS

Methanol Conversion to Light Olefins (Clarence D. Chang) (1984).
Production of Chemicals from Methanol (Warren W. Kaeding & Stephen A. Butter) (1980).

* cited by examiner

*Primary Examiner*—Thuan D. Dang
(74) *Attorney, Agent, or Firm*—Bradley Keller; Paul T. LaVoie

(57) ABSTRACT

A method for converting oxygenates to light olefins. The method comprises contacting, in a reactor, a feedstock comprising oxygenates with a molecular sieve catalyst under conditions effective to convert the feedstock to a product including light olefins and by-products, the contacting causing carbonaceous deposits to form on at least a portion of the molecular sieve catalyst producing deactivated catalyst; removing a portion of the deactivated catalyst from the reactor; regenerating the portion of the deactivated catalyst under conditions effective to remove at least a portion of the carbonaceous deposits from the deactivated catalyst to form an at least partially regenerated catalyst; exposing at least a portion of the at least partially regenerated catalyst to at least a portion of the by-products to selectivate the portion of the at least partially regenerated catalyst to form light olefins; and contacting the selectivated portion of the at least partially regenerated catalyst with the feedstock to form the product.

17 Claims, No Drawings

US 6,482,999 B2

METHOD FOR IMPROVING LIGHT OLEFIN SELECTIVITY IN AN OXYGENATE CONVERSION REACTION

FIELD OF THE INVENTION

The present invention relates to a method for increasing the selectivity to light olefins and/or for decreasing coke formation in oxygenate conversion reactions.

BACKGROUND OF THE INVENTION

Light olefins, defined herein as ethylene, propylene, and mixtures thereof, serve as feedstocks for the production of numerous important chemicals and polymers. Light olefins traditionally are produced by cracking petroleum feeds. Because of the limited supply of competitive petroleum feeds, the opportunities to produce low cost light olefins from petroleum feeds are limited. Efforts to develop light olefin production technologies, based on alternative feedstocks have increased.

An important type of alternate feedstocks for the production of light olefins are oxygenates, such as, for example, alcohols, particularly methanol and ethanol, dimethyl ether, methyl ethyl ether, diethyl ether, dimethyl carbonate, and methyl formate. Many of these oxygenates may be produced by fermentation, or from synthesis gas derived from natural gas, petroleum liquids, carbonaceous materials, including coal, recycled plastics, municipal wastes, or any organic material. Because of the wide variety of sources, alcohol, alcohol derivatives, and other oxygenates have promise as an economical, non-petroleum source for light olefin production.

The reaction, which converts oxygenates to desired light olefins, also produces by-products. Representative by-products include, for example, alkanes (methane, ethane, propane, and larger), $C_4^+$ olefins, aromatic compounds, carbon oxides and carbonaceous deposits (also referred to as "coke").

During the conversion of oxygenates to light olefins, carbonaceous deposits accumulate on the catalysts used to promote the conversion reaction. As the amount of these carbonaceous deposits increases, the catalyst begins to lose activity and, consequently, less of the feedstock is converted to the light olefin products. At some point, the build up of these carbonaceous deposits causes the catalyst to reduce its capability to convert the oxygenates to light olefins. When a catalyst can no longer convert oxygenates to olefin products, the catalyst is considered to be deactivated. Once a catalyst becomes deactivated, it must be removed from the reaction vessel and replaced with fresh catalyst. Such complete replacement of the deactivated catalyst is expensive and time consuming. To reduce catalyst costs, the carbonaceous deposits are periodically fully or partially removed from the deactivated and/or partially deactivated catalyst to allow for reuse of the catalyst. Removal of the deactivated catalyst and/or partially deactivated catalyst from the reaction process stream to remove the carbonaceous deposits is typically referred to as regeneration and is typically conducted in a unit called a regenerator.

Previously in the art, catalyst regeneration was accomplished by removing the deactivated catalyst from the process stream, removing the carbonaceous deposits from the catalyst, and then returning the regenerated catalyst to the reactor near the inlet of the reactor or reaction vessel. Conventionally, this inlet is located near the bottom quarter of the reactor or reaction vessel. By returning the regenerated catalyst near the inlet of the reactor, the regenerated catalyst would immediately contact fresh feedstock and begin conversion of the feedstock. However, doing so does nothing to control the conversion of the feedstock into by-products.

For example, U.S. Pat. No. 4,873,390 to Lewis et al. teaches a process for catalytically converting a feedstock into a product in which the feedstock is contacted with a partially regenerated catalyst. Lewis et al. describe that a partially regenerated catalyst improves the selectivity of the process to the light olefin products. While contacting the feedstock with a partially regenerated catalyst may improve the selectivity of the process to the light olefin products, it does nothing to control production of by-products.

For these reasons, a need exists in the art for improved processes which increase light olefin selectivity and control production of by-products.

SUMMARY OF THE INVENTION

The present invention solves the current needs in the art by providing a method for increasing light olefin production and controlling production of by-products.

One aspect of the present invention is directed to a method for selectivating a catalyst. As used herein, the word "selectivate" (or selectivating) refers to a process by which a certain amount of carbonaceous deposits are formed on the catalyst to cause the catalyst to produce more ethylene and propylene from the oxygenate feed and to produce fewer by-products. In the present invention, the selectivation of the catalyst occurs by contacting the catalyst with the by-products of the conversion reaction. However, the light olefins produced by the oxygenate conversion reaction can also be used for the selectivation of the catalyst, either separately or in combination with the by-products. As one well skilled in the art will appreciate, it is preferred that as much as possible of the by-products selectivate the catalyst and as little as possible of the light olefins selectivate the catalyst. As the by-products contact an at least partially regenerated catalyst, primarily the $C_4^+$ olefin portion of the by-products, is primarily converted to light olefins and carbonaceous deposits which form on the catalyst. While the accumulation of the carbonaceous deposits does contribute to the deactivation of the catalyst, the accumulation of the carbonaceous deposits also contributes to the selectivation of the catalyst. When the selectivated catalyst mixture then contacts the oxygenate feed, selectivity of the conversion reaction to forming light olefins, particularly ethylene and propylene, is increased and/or formation of by-products is reduced compared to using a fresh or regenerated catalyst that has not been selectivated according to the present invention.

The method for selectivating the catalyst comprises contacting, in a reactor, a feedstock, including oxygenate, with a molecular sieve catalyst under conditions effective to form a product including light olefins and by-products, the contacting causing carbonaceous deposits to form on at least a portion of the molecular sieve catalyst producing deactivated catalyst; removing a portion of the deactivated catalyst from the reactor; regenerating the portion of the deactivated catalyst to remove at least a portion of the carbonaceous deposits from the deactivated catalyst removed from the reactor to form an at least partially regenerated catalyst; and exposing at least a portion of the at least partially regenerated catalyst to at least a portion of the by-products to selectivate the at least partially regenerated catalyst to form light olefins. In this process, the at least partially regenerated catalyst may also be exposed to at least a portion of the light olefins to selectivate the at least partially regenerated catalyst to forming light olefins. This process may also include the step of contacting at least a portion of the selectivated at least partially regenerated catalyst with the feedstock.

Another aspect of the present invention is directed to a method for converting oxygenate to light olefins. The method comprises contacting, in a reactor, a feedstock comprising oxygenates with a molecular sieve catalyst under conditions effective to convert the feedstock to a product including light olefins and by-products, the contacting causing carbonaceous deposits to form on at least a portion of the molecular sieve catalyst producing deactivated catalyst; removing a portion of the deactivated catalyst from the reactor; regenerating the portion of the deactivated catalyst under conditions effective to remove at least a portion of the carbonaceous deposits from the deactivated catalyst to form an at least partially regenerated catalyst; exposing at least a portion of the at least partially regenerated catalyst to at least a portion of the by-products to selectivate the portion of the at least partially regenerated catalyst to form light olefins; and contacting the selectivated portion of the at least partially regenerated catalyst with the feedstock to form the product. In this method, the at least partially regenerated catalyst may also be exposed to at least a portion of the light olefins to selectivate the at least partially regenerated catalyst to forming light olefins. This method may include the additional step of recovering the light olefins. If the light olefins are recovered, then this method may also include the step of polymerizing the light olefins to form polyolefins.

Still another aspect of the present invention is directed to a method for reducing the heat of reaction in a reactor by offsetting the exothermic conversion of a feedstock during a catalyzed chemical conversion process. The method comprises contacting, in a reactor, a feedstock with a catalyst under conditions effective to form a product and by-products, the contacting causing carbonaceous deposits to form on at least a portion of the catalyst causing at least a portion of the catalyst to become deactivated catalyst; removing at least a portion the deactivated catalyst from the reactor; regenerating the portion of the deactivated catalyst removed from the reactor to remove at least a portion of the carbonaceous deposits from the deactivated catalyst to form an at least partially regenerated catalyst; and contacting the at least partially regenerated catalyst with the by-products to facilitate an endothermic reaction with the by-products.

Other advantages and uses of the process of the present invention will become apparent from the following detailed description and appended claims.

DETAILED DESCRIPTION OF THE INVENTION

When converting oxygenates to light olefins, it is desirable to maximize the production of light olefins, and to control, typically to minimize, the production of by-products. The present invention accomplishes this result by subjecting at least a portion of an at least partially deactivated catalyst to at least partial regeneration and introducing the at least partially regenerated catalyst to the conversion reactor so that the at least partially regenerated catalyst contacts at least a portion of the by-products of the oxygenate conversion reaction before the catalyst comes into contact with fresh oxygenate feed. Doing so, selectivates the catalyst to form light olefins and causes the overall process to produce fewer by-products.

The process of the present invention for converting oxygenates to light olefins employs an organic starting material (feedstock) desirably comprising oxygenates. As used herein, the term "oxygenates" is defined to include, but is not necessarily limited to, aliphatic alcohols, ethers, carbonyl compounds (aldehydes, ketones, carboxylic acids, carbonates, and the like), alkyl halides and mixtures thereof. The aliphatic moiety desirably should contain in the range of from about 1-10 carbon atoms and more desirably in the range of from about 1-4 carbon atoms. Representative oxygenates include, but are not necessarily limited to, lower straight chain or branched aliphatic alcohols, their unsaturated counterparts, and their halogen analogues. Examples of suitable compounds include, but are not necessarily limited to: methanol; ethanol; n-propanol; isopropanol; $C_4$-$C_{10}$ alcohols; methyl ethyl ether; dimethyl ether; diethyl ether; di-isopropyl ether; methyl formate; methyl chloride, methyl bromide, methyl iodide, ethyl chloride; ethyl bromide, ethyl iodide, formaldehyde; di-methyl carbonate; methyl ethyl carbonate, acetone; n-alkyl halides having n-alkyl groups of comprising the range of from about 3 to about 10 carbon atoms; and mixtures thereof. Desirably, the oxygenates used in the conversion reaction are methanol, dimethyl ether and mixtures thereof. More desirably the oxygenate is methanol. As used herein, the term "oxygenate" designates only the organic material used as the feed. The total charge of feedstock to the reaction zone may contain additional compounds, such as diluents.

In the present invention, an oxygenate feed is contacted in a reaction zone of a reactor with a molecular sieve catalyst at process conditions effective to produce light olefins, i.e., an effective temperature, pressure, WHSV (weight hourly space velocity) and, optionally, an effective amount of diluent, correlated to produce light olefins. These conditions are described in detail below. Usually, the oxygenate feed is contacted with the catalyst when the oxygenates are in a vapor phase. Alternately, the process may be carried out in a liquid or a mixed vapor/liquid phase. When the process is carried out in a liquid phase or a mixed vapor/liquid phase, different conversions and selectivities of feedstock-to-product may result depending upon the catalyst and reaction conditions. As used herein, the term reactor includes not only commercial scale reactors but also pilot sized reactor units and lab bench scale reactor units.

In a steady state or a semi-steady state in the reactor, a mixture of a partially deactivated catalyst fraction, a deactivated catalyst fraction and a partially or fully regenerated catalyst fraction are typically present in the reactor. As used herein and in the claims, the term "deactivated" includes both partially deactivated catalyst and fully deactivated catalyst. In order to form a desired catalyst mixture, a portion of the deactivated catalyst from the reactor is removed from the reactor, separated from products, and sent to the regenerator. In the regenerator, the carbonaceous deposits are removed from the catalyst. While it is theoretically possible to remove all of the carbonaceous deposits from the catalyst, such an activity may not be practical due to time constraints and costs of continued regeneration. For those reasons, as much as possible of the carbonaceous deposits are removed from the catalyst. In other words, the catalyst is at least partially regenerated. However, the catalyst is, desirably, regenerated as fully and completely as practical. The remainder of the deactivated catalyst remains in the reactor. Desirably, a portion of catalyst is removed from the reactor for regeneration and recirculation back to the reactor at a rate of from about 0.1 times to about 10 times, desirably from about 0.2 times to about 5 times, and most desirably from about 0.3 to about 3 times the total feed rate of oxygenates to the reactor.

It has been found in the present invention that the use of an at least partially regenerated catalyst provides better light olefin selectivity with reasonable catalyst activity, and provides better control of the reaction temperature inside of the reactor than prior art processes. In the present invention, the amount of coke residue or carbonaceous deposits remaining on the catalyst after partial regeneration ranges from about 0.1 wt % to 95 wt %, desirably from about 0.5 wt % to about 85 wt %, and more desirably from about 1 wt % to about 65 wt % of the original amount of coke residue or carbonaceous deposits present on the deactivated catalyst. The catalyst may also be fully regenerated. For the purposes of this application, the phrase "fully regenerated" means that no more than about 0.1 wt % of the carbonaceous deposits remain on the catalyst. The regeneration temperature in the catalyst regenerator measures from about 250° C. to about 750° C. and desirably from about 300° C. to about 700° C. Desirably, the catalyst regenerator includes a catalyst separator, desirably a plurality of cyclones, to separate flue gases from the catalyst.

Desirably, the regeneration is carried out in the presence of a gas comprising oxygen or other oxidants. Examples of other oxidants include, but are not necessarily limited to singlet $O_2$, $O_3$, $SO_3$, $N_2O$, NO, $NO_2$, $N_2O_5$, and mixtures thereof. Air and air diluted with steam, nitrogen and/or $CO_2$ are desired regeneration gases. Desirably, the oxygen concentration in the regenerator is reduced to a controlled level to minimize overheating or the creation of hot spots in the spent or deactivated catalyst. The deactivated catalyst also may be regenerated reductively with hydrogen, carbon monoxide, mixtures of hydrogen and carbon monoxide, or other suitable reducing agents and gases. Depending on the other oxygenate conversion reaction parameters and the feedstock, a combination of an oxidative regeneration and a reductive regeneration can be employed.

Before the deactivated catalyst is at least partially regenerated, especially oxidatively regenerated, at least some of the volatile organics are desirably stripped from the catalyst in a stripper or stripping chamber, using steam, nitrogen, or methane, among others. Stripping the catalyst may improve the process economics, process operation and/or emission control. If the organics are not removed, they will provide at most fuel value. With removal, the recovered organics may have a higher value as chemicals, not as fuels. In addition, the amount of organics removed during regeneration or partial regeneration is reduced. This leads to better heat management both in the catalyst regenerator and on the catalyst, particularly when an oxidative regeneration method is used. Less carbon oxides are generated in an oxidative regeneration mode because there are less organics to be oxidatively removed.

After being regenerated, and optionally stripped, the at least partially regenerated catalyst is exposed to at least the by-products of the conversion reaction. The at least partially regenerated catalyst may also be exposed to the light olefins produced by the conversion reaction or a mixture of the by-products and the light olefins. This exposure occurs either in the reactor or in a vessel separate from the reactor. Prior to being exposed to the oxygenate feedstock, the at least partially regenerated catalyst fraction contacts, at a suitable concentration and/or partial pressure, the by-products, and optionally the light olefins, for a time period sufficient and/or conditions effective to selectivate the regenerated catalyst. This initial contact with the by-products, and optionally the light olefins, may be either inside or outside of the reactor. Desirably, the initial contact is achieved by sending the at least partially regenerated catalyst, at a suitable temperature, to a location in the reactor which contains mostly the by-products, and optionally the light olefins. This portion of the reactor may also contain either the non-regenerated, deactivated portion of the catalyst, an amount of the unreacted oxygenate feed or a combination of both. This contact with the by-products, and optionally the products, of the conversion reaction serves to selectivate the at least partially regenerated catalyst to forming light olefins. The selectivated catalyst is then mixed with the rest of the at least partially deactivated catalyst to form a mixture of the nonregenerated catalyst and the selectivated catalyst, followed by contacting the catalyst mixture with the feedstock.

Desirably, the at least partially regenerated catalyst is returned to contact the by-products, and optionally the light olefins, when the at least partially regenerated catalyst is hot. By "hot" it is meant that at least the catalyst from the regenerator is not cooled below the temperature of the catalyst already in the reactor prior to being contacted with the by-products, and optionally the products. For example, catalyst being returned from the regenerator will have a temperature of from about 250° C. to about 750° C. One skilled in the art will appreciate that a slight amount of cooling may take place as the catalyst is transferred from the regenerator to the reactor. Hot catalyst can be used because the at least partially regenerated catalyst is not initially contacting the full amount of the oxygenated feedstock but instead the products of the converted feed and higher temperatures can be used to facilitate conversion of $C_4^+$ olefins. One skilled in the art will appreciate that the at least partially regenerated catalyst will contact some unconverted feed but will not contact enough of the pure feed to reduce the beneficial effects of contacting the at least partially regenerated catalyst with the by-products.

When the oxygenate conversion reaction of the present invention is conducted in a fluidized bed reactor which has a riser (or riser region) and a dense fluid bed section (or dense phase region), the at least partially regenerated catalyst is returned to one of the following locations in the reactor: above the dense phase region; immediately below the dense phase region; or anywhere between about the top one fourth of the riser region and the dense phase region, desirably between about the top one-fourth of the riser region and about the bottom one fourth of the dense phase region.

In another embodiment of the process of the present invention, the contact between the by-products, and optionally the light olefins or a mixture thereof, of the oxygenate conversion reactor and the at least partially regenerated catalyst fraction to selectivate the catalyst may occur in a separate vessel outside of the reactor. The temperature, pressure, time period, and other reaction conditions effective for the initial contact are determined by factors including, but not necessarily limited to, the oxygenate conversion reaction conditions, the amount of residual carbonaceous materials present on the catalyst, the level or degree of the at least partial regeneration, percent of total coke removed from the deactivated catalyst, the oxygenate feed selected, overall heat integration considerations, and combinations thereof. Quite a bit of flexibility exists in selecting the parameters to achieve the desired results. Again, it is desirable to contact the catalyst with the products of the conversion reaction while the catalyst is hot.

Once the at least partially regenerated catalyst has been selectivated, the selectivated catalyst may then be exposed to the oxygenate feed to convert the oxygenate feed to olefin products and the by-products. As stated above, the contacting of the oxygenate feedstock with the selectivated catalyst increases the selectivity of the oxygenate conversion reaction to producing light olefins.

In the oxygenation conversion reaction of the present invention, the temperature useful to convert the oxygenate feed to the products varies over a wide range depending, at least in part, on the selected catalyst, the fraction of the regenerated catalyst in the catalyst mixture, and the reactor configuration. Although not limited to a particular temperature, best results are obtained if the process is conducted at a temperature from about 200° C. to about 700° C., desirably from about 250° C. to about 600° C., and most desirably from about 300° C. to about 500° C. Lower temperatures generally result in lower rates of reaction, and the formation rate of the desired light olefin products may become markedly slower. However, at higher temperatures, the process may not form an optimum amount of light olefin products, and the coking rate may become too high.

Light olefins form, although not necessarily in optimum amounts, at a wide range of pressures including, but not limited to, autogeneous pressures and pressures in the range of from about 0.1 kPa to about 5 MPa. A desired pressure is from about 5 kPa to about 1 MPa and most desirably from about 20 kPa to about 500 kPa. The foregoing pressures do not include that of a diluent, if any, and refer to the partial pressure of the feedstock as it relates to oxygenate compounds and/or mixtures thereof. Pressures outside of the stated ranges may be used and are not excluded from the scope of the invention. Lower and upper extremes of pressure may adversely affect selectivity, conversion, coking rate, and/or reaction rate; however, light olefins will still form.

If desired, the oxygenate conversion reaction may be continued for a period of time sufficient to produce light olefins and/or to reach a steady state of production of light olefin products. It is also desirable to match the catalyst regeneration cycle and the oxygenate conversion reaction to achieve the desired catalytic performance, such as activity maintenance, light olefin selectivity and control of by-products. In addition, a portion of the catalyst may be recirculated in the reactor before it is sent to the regenerator. Because at least some attrition occurs, a certain amount of replacement catalyst is used to replace the catalyst fines generated and separated.

A wide range of weight hourly space velocities (WHSV) for the feedstock, defined as weight feed per hour per weight of catalyst, function with the present invention. The WHSV should be high enough to maintain the catalyst in the fluidized state under the reaction conditions and within the reactor configuration and design. Generally, the WHSV is from about 1 $hr^{-1}$ to about 5000 $hr^{-1}$, desirably from about 2 $hr^{-1}$ to about 3000 $hr^{-1}$, and most desirably from about 5 $hr^{-1}$ to about 1500 $hr^{-1}$. For a feedstock comprising methanol, dimethyl ether, or mixtures thereof, the WHSV is most desirably in the range of from about 5 $hr^{-1}$ to about 300 $hr^{-1}$. Because the catalyst may contain other materials which act as inerts, fillers, or binders, the WHSV is calculated on the weight basis of oxygenates in the feedstock and the molecular sieve content of the catalyst.

One or more diluents may be fed to the reaction zone with the oxygenates, such that the total feed mixture comprises diluent in a range of from about 1 mol % and about 99 mol %. Diluents also may be used in connection with recharging the at least partially regenerated catalyst back to the reactor. Diluents which may be employed in the process include, but are not necessarily limited to, water (steam), nitrogen, carbon dioxide, carbon monoxide, hydrogen, helium, argon, paraffins, light saturated hydrocarbons (such as methane, ethane, and propane), aromatic compounds, and mixtures thereof. Desired diluents are water (steam), nitrogen, and mixtures thereof.

The level of conversion of the oxygenates—particularly during a steady state of the reaction—can be maintained to reduce the level of unwanted by-products. Conversion can also be maintained sufficiently high to avoid the need for commercially unacceptable levels of recycling of unreacted feeds. A reduction in unwanted by-products is seen when conversion moves from 100 mol % to about 98 mol % or less. Recycling up to as much as about 50 mol % of the feedstock is commercially acceptable. Therefore, conversions levels which achieve both goals are from about 50 mol % to about 98 mol % and, desirably, from about 85 mol % to about 98 mol %. However, it is also acceptable to achieve conversion between 98 mol % and 100 mol % in order to simplify the recycling process. Oxygenate conversion may be maintained at this level using a number of methods familiar to persons of ordinary skill in the art. Examples include, but are not necessarily limited to, adjusting one or more of the following: the reaction temperature, pressure, flow rate (i.e., space velocity); level and degree of catalyst regeneration; amount of catalyst re-circulation; the specific reactor configuration; the feed composition; and other parameters which affect the conversion.

Fixed beds may also be used to practice the process of the present invention, but are less desirable because an oxygenate-to-olefin conversion reaction run in such a reactor requires several stages with intercoolers or other heat removal devices because of the exothermicity of the reaction. Further, the oxygenate conversion reaction also results in a high pressure drop in a fixed bed due to the production of low pressure, low density gases. In addition, the processes of removing the deactivated catalyst and recharging the at least partially regenerated catalyst are difficult to perform.

Catalysts suitable for catalyzing the oxygenate-to-olefin conversion reaction of the present invention include molecular sieve catalysts. Molecular sieve catalysts can be zeolitic (zeolites) or non-zeolitic (non-zeolites). Useful catalysts may also be formed from mixtures of zeolitic and non-zeolitic molecular sieve catalysts. Desirably, the catalyst is a non-zeolitic molecular sieve. Desired catalysts for use with the process of the present invention include "small" and "medium" pore molecular sieve catalysts. "Small pore" molecular sieve catalysts are defined as catalysts with pores having a diameter of less than about 5.0 Angstroms. "Medium pore" molecular sieve catalysts are defined as catalysts with pores having a diameter in the range of from about 5.0 to about 10.0 Angstroms. Properly adjusted acid strength, acidity distribution, and acid site density are also keys to a good oxygenate conversion catalyst.

Useful zeolitic molecular sieve catalysts include, but are not limited to, mordenite, chabazite, erionite, ZSM-5, ZSM-34, ZSM-48 and mixtures thereof. Methods of making these catalysts are known in the art and need not be discussed here.

Silicoaluminophosphates ("SAPOs") are one group of non-zeolitic molecular sieve catalysts that are useful in the present invention. Processes for making useful SAPOs are known in the art. In particular, small pore SAPOs are desired. SAPO type molecular sieves have a three-dimensional microporous crystalline framework of $PO_2^+$, $AlO_2^-$, $SiO_2$ and $MeO_2^m$ tetrahedral units, with or without metals in the framework. The "m" superscript represents a net electric charge depending on the valence state of the substituent, Me. When "Me" has valence state of +2, +3, +4, +5, or +6 valence state, m is −2, −1, 0, +1, and +2, respectively. "Me" includes, but is not necessarily limited to, Zn, Mg, Mn, Co, Ni, Ga, Fe, Ti, Zr, Ge, Sn, Cr, and mixtures thereof. Because an aluminophosphate ($AlPO_4$) framework inherently is neutral in electrical charges, the incorporation of silicon or other metallic or nonmetallic elements into the framework by substitution generates more active catalytic sites, particularly acid sites, and increased acidity. Controlling the quantity and location of silicon atoms and other elements incorporated into an $AlPO_4$ framework is important in determining the catalytic properties of a particular SAPO-type molecular sieve. Suitable SAPOs for use in the invention include, but are not necessarily limited to, SAPO-34, SAPO-17, SAPO-18, SAPO-44, SAPO-56 and mixtures thereof. In a more desired embodiment, the SAPO is SAPO-34.

Substituted SAPOs form a class of molecular sieves known as "MeAPSOs," which are also useful in the present invention. Processes for making MeAPSOs are known in the art. SAPOs with substituents, such as MeAPSOs, also may be suitable for use in the present invention. Suitable substituents, "Me," include, but are not necessarily limited to, nickel, cobalt, manganese, zinc, titanium, strontium, magnesium, barium, and calcium. The substituents may be incorporated during synthesis of the MeAPSOs. Alternately, the substituents may be incorporated after synthesis of SAPOs or MeAPSOs using many methods. The methods include, but are not necessarily limited to ion-exchange, incipient wetness, dry mixing, wet mixing, mechanical mixing, and combinations thereof.

Desired MeAPSOs are small pore MeAPSOs having pore size smaller than about 5 Angstroms. Small pore MeAPSOs include, but are not necessarily limited to NiSAPO-34, CoSAPO-34, NiSAPO-17, CoSAPO-17, and mixtures thereof.

Aluminophosphates (ALPOs) with substituents, also known as "MeAPOs," are another group of molecular sieves that may be suitable for use in the present invention, with desired MeAPOs being small pore MeAPOs. Processes for making MeAPOs are known in the art. Suitable substituents include, but are not necessarily limited to nickel, cobalt, manganese, zinc, titanium, strontium, magnesium, barium, and calcium. The substituents may be incorporated during synthesis of the MeAPOs. Alternately, the substituents may be incorporated after synthesis of ALPOs or MeAPOs using many methods. The methods include, but are not necessarily limited to ion-exchange, incipient wetness, dry mixing, wet mixing, mechanical mixing, and combinations thereof. The catalyst may be incorporated into a solid composition, preferably solid particles, in which the catalyst is present in an amount effective to promote the desired conversion reaction. The solid particles may include a catalytically effective amount of the catalyst and matrix material, preferably at least one of a filler material and a binder material, to provide a desired property or properties, e.g., desired catalyst dilution, mechanical strength and the like, to the solid composition. Such matrix materials are often to some extent porous in nature and often have some nonselective catalytic activity to promote the formation of undesired products and may or may not be effective to promote the desired chemical conversion. Such matrix, e.g., filler and binder, materials include, for example, synthetic and naturally occurring substances, metal oxides, clays, silicas, aluminas, silica-aluminas, silica-magnesias, silica-zirconias, silica-thorias, silica-berylias, silica-titanias, silica-alumina-thorias, silica-aluminazirconias, and mixtures of these.

The solid particles preferably comprise about 1% to about 99%, more preferably about 5% to about 90% and still more preferably about 10% to about 80%, by weight of catalyst; and an amount of about 1% to about 99%, more preferably about 5% to about 90% and still more preferably about 10% to about 80%, by weight of matrix material.

The preparation of solid compositions, e.g., solid particles, comprising the catalyst and matrix material, is conventional and well known in the art and, therefore, is not discussed in detail here.

The present invention will be better understood with reference to the following examples, which illustrate, but are not intended to limit the present invention.

EXAMPLE 1

A 0.055 g sample of SAPO-34 catalyst that had previously been calcined in air at 550° C. for 16 hours was placed between two quartz wool plugs in a 4 mm diameter quartz reactor tube. The tube was then inserted into an electrically heated zone which was directly linked to a gas chromatograph for on-line analyses of products. The pressure inside of the reactor tube was maintained at 16.5 psig by using a back-pressure regulator. The temperature was maintained at 450±2° C. Helium was used as a carrier gas at a flow rate of 60 ml/min. One milliliter (ml) gas samples of ethylene ($C_2^=$) were injected successively at 30 minute intervals onto the catalyst. The products in the effluent were directed to a gas chromatographic column for analyses. The ethylene conversion was calculated by subtracting from 100% all of the detected gas phase hydrocarbon products other than ethylene feed itself. Selectivities to the products of interest are shown in Table I. Coke yield was not determined.

EXAMPLE 2

The procedure described in EXAMPLE 1 was repeated except that one milliliter (ml) gas samples of propylene ($C_3^=$) were used as feed. The propylene conversion was calculated by subtracting from 100% all of the detected gas phase hydrocarbon products other than propylene feed itself. Selectivities to the products of interest are shown in Table I. Coke yield was not determined.

EXAMPLE 3

The procedure described in EXAMPLE 1 was repeated except that one milliliter (ml) gas samples of 1-butene ($1$-n-$C_4^=$) were used as feed. The butene-1 conversion was calculated by subtracting from 100% all of the detected gas phase hydrocarbon products other than butene-1 feed and other butene isomers. Selectivities to the products of interest are shown in Table I. Coke yield was not determined.

EXAMPLE 4

The procedure described in EXAMPLE 1 was repeated except that one microliter ($\mu$l) liquid samples of 1-pentene ($1$-n-$C_5^=$) were used as feed. The pentene-1 conversion was calculated by subtracting from 100% all of the detected gas phase hydrocarbon products other than butene-1 feed and other $C5^+$ compounds. Selectivities to the products of interest are shown in Table I. Coke selectivity was not determined in this example.

EXAMPLE 5

The procedure described in EXAMPLE 1 was repeated except that one microliter ($\mu$l) liquid samples of 1-heptene ($1$-n-$C_7^=$) were used as feed. The heptene-1 conversion was calculated by subtracting from 100% all of the detected gas phase hydrocarbon products other than heptene-1 feed and other C5+ compounds. Selectivities to the products of interest are shown in Table I. Coke selectivity was not determined in this example.

EXAMPLE 6

The procedure described in EXAMPLE 3 was repeated except that the reaction temperature was maintained at 500° C. The butene conversion was calculated by subtracting from 100% all of the detected gas phase hydrocarbon products other than butene-1 feed itself and other butene isomers. Selectivities to the products of interest are shown in Table I. Coke selectivity was not determined in this example.

TABLE I

| Example | Feed | Conversion (%) | Selectivity (%) | | | | Relative Rxn Rate* |
|---|---|---|---|---|---|---|---|
| | | | $C_2^=$ | $C_3^=$ | $C_4^=$ | $C_5^{=+}$ | |
| 1 | $C_2^=$ | 2.2 | N.A. | 55.3 | 14.7 | 6.6 | 1 |
| 2 | $C_3^=$ | 22.8 | 15.3 | N.A. | 56.6 | 11.8 | 12 |
| 3 | 1-n-$C_4^=$ | 31.5 | 9.8 | 66.0 | N.A. | 13.8 | 17 |
| 4 | 1-n-$C_5^=$ | 13.3 | 11.4 | 45.2 | 41.1 | N.A. | 6 |
| 5 | 1-n-$C_7^=$ | 52.6 | 1.4 | 47.0 | 51.0 | N.A. | 33 |
| 6 | 1-n-$C_4^=$ @ 500° C. | 45.7 | 15.8 | 66.3 | N.A. | 15.5 | 27 |

*The reaction rates were calculated based on first order reaction rates and weight hourly space velocities (WHSV) were estimated. The rates are expressed as relative rates to the ethylene reaction rate, which is set as 1, in order to mitigate any potential WHSV measurement inaccuracies.

The results in Table I show that ethylene is relatively unreactive under typical oxygenate conversion conditions. The relative reaction rates of converting $C_3^=$ to $C_7^=$ were at least six times faster than the rate of converting ethylene. Accordingly, longer chain olefins are preferentially converted to shorter chain olefins when contacting a non-zeolitic molecular sieve catalyst such as SAPO-34. When a regenerated catalyst is sent back to the reactor, it is advantageous to expose the regenerated catalyst to the oxygenate conversion products first to further convert heavier olefins to ethylene and/or propylene. This method, in effect, increases the overall yield or selectivity of the desired light olefins and reduces the amount of heavier olefins.

Example 6 shows a much higher reaction rate of converting butenes to light olefins by contacting with an oxygenate conversion catalyst at a higher temperature without adversely affecting the selectivities to ethylene and propylene.

One skilled in the art will appreciate that the light olefins produced by the oxygenate-to-olefin conversion reaction of the present invention can be polymerized to form polyolefins. Processes for forming polyolefins from olefins are known in the art. Prior to being subjected to a polymerization process, the olefin products are recovered from the products of the oxygenate-to-olefin conversion reaction.

As stated above, the preferred oxygenate for use in the methods of the present invention is methanol. Each of the methods of the present invention may also include the step of forming methanol. Methods for forming oxygenates, such as methanol, are known in the art and will not be discussed in detail here. Two methods for forming oxygenates include fermentation and formation from synthesis gas. These methods are also useful to form other oxygenates.

As also stated above, the at least partially regenerated catalyst can be used to manage heat within the conversion reactor. As one skilled in the art will appreciate, the conversion of the oxygenate feedstock to light olefins is an exothermal reaction. By returning the at least partially regenerated catalyst to contact the by-products of the conversion reaction, the longer chain by-products of the conversion reaction are converted to shorter chain light olefin products. The conversion of the longer chain by-products to shorter chain light olefin products is an endothermic reaction. The conversion of the by-products into light olefin products consumes heat produced by the conversion of the oxygenate feed, thus, reducing the overall heat of reaction in a reactor during a catalyzed chemical conversion process. By feeding the hot catalyst to the reactor, a catalyst cooler may be eliminated from the apparatus used to produce the desired olefins or, at least, the catalyst cooler can be reduced in size and/or cooling duty. The hot catalyst is cooled in the reactor by the endothermic conversion of the longer chain ($C_4$, $C_5$, $C_6$ and longer) olefins into ethylene, propylene and coke.

Persons of ordinary skill in the art will recognize that many modifications may be made to the present invention without departing from the spirit and scope of the present invention. The embodiment described herein is meant to be illustrative only and should not be taken as limiting the invention, which is defined by the following claims.

What is claimed is:

1. A method for improving the selectivity of light olefins in the process for converting oxygenate feedstocks to olefins, comprising:

contacting an oxygenate feedstock with a molecular sieve catalyst under conditions effective to produce a product stream comprising $C_2$–$C_4$ olefins;

forming carbonaceous deposits on at least a portion of the molecular sieve catalyst, thereby forming a deactivated catalyst;

regenerating at least a portion of the deactivated catalyst under conditions effective to remove at least a portion of the carbonaceous deposits from the portion of deactivated catalyst, thereby forming a regenerated catalyst; and contacting at least a portion of the regenerated catalyst with at least a portion of the product stream including the $C_2$–$C_4$ olefins to form a selectivated catalyst.

2. The method of claim 1 further comprising contacting at least a portion of the selectivated catalyst with the oxygenate feedstock.

3. The method of claim 1 wherein the oxygenate feedstock is selected from methanol, ethanol, n-propanol, isopropanol; C4–C10 alcohols, methyl ethyl ether; dimethyl ether; diethyl ether; di-isopropyl ether; methyl formate; methyl chloride; methyl bromide; methyl iodide; ethyl chloride; ethyl bromide; ethyl iodide; formaldehyde; di-methyl carbonate; methyl ethyl carbonate; acetone; n-alkyl halides having n-akyl groups of from about 3 to about 10 carbon atoms; and mixtures thereof.

4. The method of claim 3 wherein the oxygenate feedstock comprises methanol.

5. The method of claim 3 wherein the oxygenate feedstock further comprises from about 1 mol % to about 99 mol % of a diluent.

6. The method of claim 5 wherein the diluent is selected from water, nitrogen, carbon dioxide, carbon monoxide, hydrogen, helium, argon, parrafins, saturated hydrocarbons, aromatic hydrocarbonds, and mixtures thereof.

7. The method of claim 6 wherein the diluent comprises water.

8. The method of claim 1 wherein the the regenerated catalyst has a carbonaceous carbon content of from about 0.1%, by weight, to about 95%, by weight, relative to the carbonaceous carbon content of the deactivated catalyst.

9. The method of claim 8 wherein the regenerated catalyst has a carbonaceous carbon content of from about 0.5%, by weight, to about 85%, by weight, relative to the carbonaceous carbon content of the deactivated catalyst.

10. The method of claim 9 wherein the regenerated catalyst has a carbonaceous deposit content of from about 1%, by weight, to about 65%, by weight, relative to the carbonaceous carbon content of the deactivated catalyst.

11. The method of claim 1 wherein the regenerating is carried out at a temperature of from about 250° C. to about 750° C.

12. The method of claim 11 wherein the regenerating is carried out at a temperature of from about 300° C. to about 700° C.

13. The method of claim 1 wherein the molecular sieve catalyst has a pore size of from about 5 to about 10 angstroms.

14. The method of claim 1 wherein the molecular sieve catalyst is selected from one or more silicoaluminophosphates, metal containing forms thereof, and mixtures thereof.

15. The method of claim 14 wherein the molecular sieve catalyst is selected from SAPO-11, SAPO-17, SAPO-18, SAPO-34, SAPO-44, SAPO-56, metal containing forms thereof, and mixtures thereof.

16. The method of claim 15 wherein the molecular sieve catalyst comprises SAPO-34.

17. A method for improving the selectivity of light olefins in the process for converting oxygenate feedstocks to olefins, comprising:

contacting an oxygenate feedstock comprising water and methanol with a silicoaluminophosphate molecular sieve catalyst at a temperature of from about 200° C. to about 700° C. and a feedstock weight hourly space velocity of from about 1 $hr^{-1}$ to about 5000 $hr^{-1}$ to produce a products stream comprising $C_2$–$C_4$ olefins;

forming carbonaceous deposits on at least a portion of the silicoaluminophosphate molecular sieve catalyst, thereby forming a deactivated catalyst;

regenerating at least a portion of the deactiveated catalyst under conditions effective to remove at least a portion of the carbonaceous deposits from the portion of deactivated catalyst, thereby forming a regenerated catalyst;

contacting at least a portion of the regenerated catalyst with at least a portion of the product stream including the $C_2$–$C_4$ olefins to form a selectivated catalyst; and contacting at least a portion of the selectivated catalyst with the oxygenate feedstock.

\* \* \* \* \*